United States Patent
Irie et al.

(10) Patent No.: US 7,052,518 B2
(45) Date of Patent: May 30, 2006

(54) ARTIFICIAL BONE AND TISSUE ENGINEERING CARRIER

(75) Inventors: Hiroyuki Irie, Akishima (JP); Hikaru Inoue, Higashimurayama (JP)

(73) Assignee: Olympus Corporation, Tokyo (JP)

( * ) Notice: Subject to any disclaimer, the term of this patent is extended or adjusted under 35 U.S.C. 154(b) by 23 days.

(21) Appl. No.: 10/664,756

(22) Filed: Sep. 18, 2003

(65) Prior Publication Data

US 2004/0064194 A1   Apr. 1, 2004

(51) Int. Cl.
   *A61F 2/28*   (2006.01)
(52) U.S. Cl. ............... 623/23.56; 623/23.76; 623/23.5
(58) Field of Classification Search ............ 623/23.56, 623/23.6, 23.61, 23.5–23.55, 929, 924, 914; 424/549

See application file for complete search history.

(56) References Cited

U.S. PATENT DOCUMENTS

| | | | | |
|---|---|---|---|---|
| 5,531,794 A | * | 7/1996 | Takagi et al. ............. | 623/23.56 |
| 5,939,323 A | | 8/1999 | Valentini et al. | |
| 6,316,091 B1 | | 11/2001 | Richart et al. | |
| 6,821,916 B1 | * | 11/2004 | Myoi et al. .................... | 501/1 |
| 2002/0037799 A1 | | 3/2002 | Li et al. | |
| 2002/0052662 A1 | * | 5/2002 | Imura et al. ............. | 623/23.56 |
| 2003/0171822 A1 | * | 9/2003 | Lo .......................... | 623/23.56 |

FOREIGN PATENT DOCUMENTS

| | | |
|---|---|---|
| JP | 63-040782 | 2/1988 |
| JP | 07-194688 | 8/1995 |
| JP | 2000-302567 | 10/2000 |
| JP | 2002-017846 | 1/2002 |
| WO | WO 00/45867 | 8/2000 |
| WO | WO 01/94274 A1 | 12/2001 |
| WO | WO 02/076522 A1 | 10/2002 |

OTHER PUBLICATIONS

Uemura, Toshimasa et al., "Transplatation of cultured bone cells using combinations of scaffolds and culture techniques", Biomaterials (2003), vol. 24, No. 13, pp. 2277-2286.

Jun, Youn-Ki et al., "The fabrication and biochemical evaluation of alumina reinforced calcium phosphate porous implants", Biomaterials (2003), vol. 24, No. 21, pp. 3731-3739.

Dong, Jian et al., "In vivo evaluation of a novel porous hydroxyapatite to sustain osteogenesis of transplanted bone marrow-derived osteoblastic cells", Journal of Biomedical Materials Research (2001), vol. 57, No. 2, pp. 208-216.

(Continued)

*Primary Examiner*—Alvin J. Stewart
(74) *Attorney, Agent, or Firm*—Scully, Scott, Murphy & Presser, P.C.

(57) ABSTRACT

An artificial bone comprising a calcium phosphate-based ceramic porous body having a plurality of pores which are three-dimensionally distributed throughout an entire region of the porous body including a surface thereof and have a diameter ranging from 0.01 μm to 2000 μm, and interconnecting portions which are formed between neighboring pores, interconnect a plurality of pores existing on a surface of the porous body.

10 Claims, 2 Drawing Sheets

OTHER PUBLICATIONS

Ripamonti, U., "Calvarial reconstruction in baboons with porous hydroxyapatite", Database Medline/U.S. National Library of Medicine (1992); and The Journal of Craniofacial Surgery (1992), vol. 3, No. 3, pp. 149-159.

Okura, T., et al., "Development of Bone Compensation Agent Citrate R Air Hole Porous Body", Fine Ceram rep., 16(7), pp. 156-157, Jul. 1998.

* cited by examiner

ARTIFICIAL BONE AND TISSUE ENGINEERING CARRIER

BACKGROUND OF THE INVENTION

1. Field of the Invention

The present invention relates to an artificial bone and to a tissue engineering carrier.

2. Description of the Related Art

It is known in the art of plastic surgery to employ autogenetic bone graft as an orthodox method in the restoration of defective bone. The autogenetic bone graft is considered highly reliable considering the past operating experience thereof, but this autogenetic bone graft is accompanied with various problems that the quantity of collectable bone is limited, that the healthy bone is invaded due to the collection of bone, and that the operation of the transplantation takes relatively long time.

Because of these problems, there has been developed a method of employing an artificial bone in recent years, wherein a porous body containing calcium phosphate as a main component is employed as the artificial bone. This method of employing an artificial bone is now widely employed as means for overcoming the aforementioned problems involved in the autogenetic bone graft.

Living bone contains, as a main component, calcium phosphate as an inorganic component. The calcium phosphate compound generally has bone conducting property which is the nature of living cell to form bone by taking advantage of the calcium phosphate compound. Accordingly, the artificial bone is generally designed to form a porous material containing the calcium phosphate compound as a main component and constituted by a bone structure throughout the porous material.

The features of the porous material for constituting the artificial bone are very important for enabling the bone structure to be quickly formed throughout the entire region of the repairing portion, particularly the inner or core portion of the artificial bone. For example, JP Laid-open Patent Publication (Kokai) No. 2000-302567 discloses a calcium phosphate porous body having interconnected pores, an average diameter of the interconnected portions of the pores being 50 µm or more and an average diameter of the pores being 150 µm or more.

BRIEF SUMMARY OF THE INVENTION

According to one aspect of the present invention, there is provided an artificial bone comprising a calcium phosphate-based ceramic porous body having a plurality of pores which are three-dimensionally distributed throughout an entire region of the porous body including a surface thereof and each has a diameter ranging from 0.01 µm to 2000 µm, and interconnecting portions which are formed between neighboring pores, interconnect a plurality of pores existing on a surface of the porous body, and each has a diameter of 100 µm or more.

This artificial bone can be preferably employed as a tissue engineering carrier.

According to a second aspect of the present invention, there is provided an artificial bone comprising a calcium phosphate-based ceramic porous body having a plurality of spherical or amoeba-like pores which are three-dimensionally distributed throughout an entire region of the porous body, are interconnected with each other, and each has a diameter ranging from 0.01 µm to 2000 µm, the porous body having a porous structure in which a total volume "A" of pores which are interconnected with each other through an interconnecting portion having a diameter of 100 µm or more from a core portion to outer surface portion of the porous body is accounted for 5% or more based on an entire volume of the porous body and the total volume "A" is accounted for 25% or more based on a total volume of the pores having a pore diameter of 10 µm or more in the porous body, or a porous structure in which a total volume of the pores interconnected with each other through an interconnecting portion having a diameter of "B" µm or more from a core portion to outer surface portion of the porous body among the pores interconnected with each other through an interconnecting portion having a diameter of 5 µm or more is defined as "C", and a maximum value of differential dC/dB is derived under a condition of: B>100 µM.

In this artificial bone, at least one substance selected from the group consisting of BMP, FGF, TGF-β, PDGF, VEGF, IGF, HGF, PTH and estrogen may be incorporated in the calcium phosphate-based ceramic porous body.

Further, according to a third aspect of the present invention, there is provided a tissue engineering carrier which is capable of tissue-engineeringly incorporating living cells, and comprises a calcium phosphate-based ceramic porous body having a plurality of spherical or amoeba-like pores which are three-dimensionally distributed throughout an entire region of the porous body, are interconnected with each other, and each has a diameter ranging from 0.01 µm to 2000 µm, the porous body having a porous structure in which a total volume "A" of pores which are inter-connected with each other through an interconnecting portion having a diameter of 100 µm or more from a core portion to outer surface portion of the porous body is accounted for 5% or more based on an entire volume of the porous body and the total volume "A" is accounted for 25% or more based on a total volume of the pores having a pore diameter of 10 µm or more in the porous body, or a porous structure in which a total volume of the pores interconnected with each other through an interconnecting portion having a diameter of "B" µm or more from a core portion to outer surface portion of the porous body among the pores interconnected with each other through an interconnecting portion having a diameter of 5 µm or more is defined as "C", and a maximum value of differential dC/dB is derived under a condition of: B>100 µm.

Further, according to a fourth aspect of the present invention, there is provided an artificial bone wherein at least one kind of cell selected from the group consisting of stem cell, marrow anaplostic cell, osteoblast, precursor cell of osteoblast, osteoclast and precursor cell of osteoclast is incorporated in the aforementioned tissue engineering carrier.

In the aforementioned artificial bone, the calcium phosphate-based ceramic may be preferably selected from the group consisting of β-tricalcium phosphate, apatite hydroxide, ceramics comprising β-tricalcium phosphate and apatite hydroxide, and crystallized glass.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodi

DETAILED DESCRIPTION OF THE INVENTION

Figure 1:
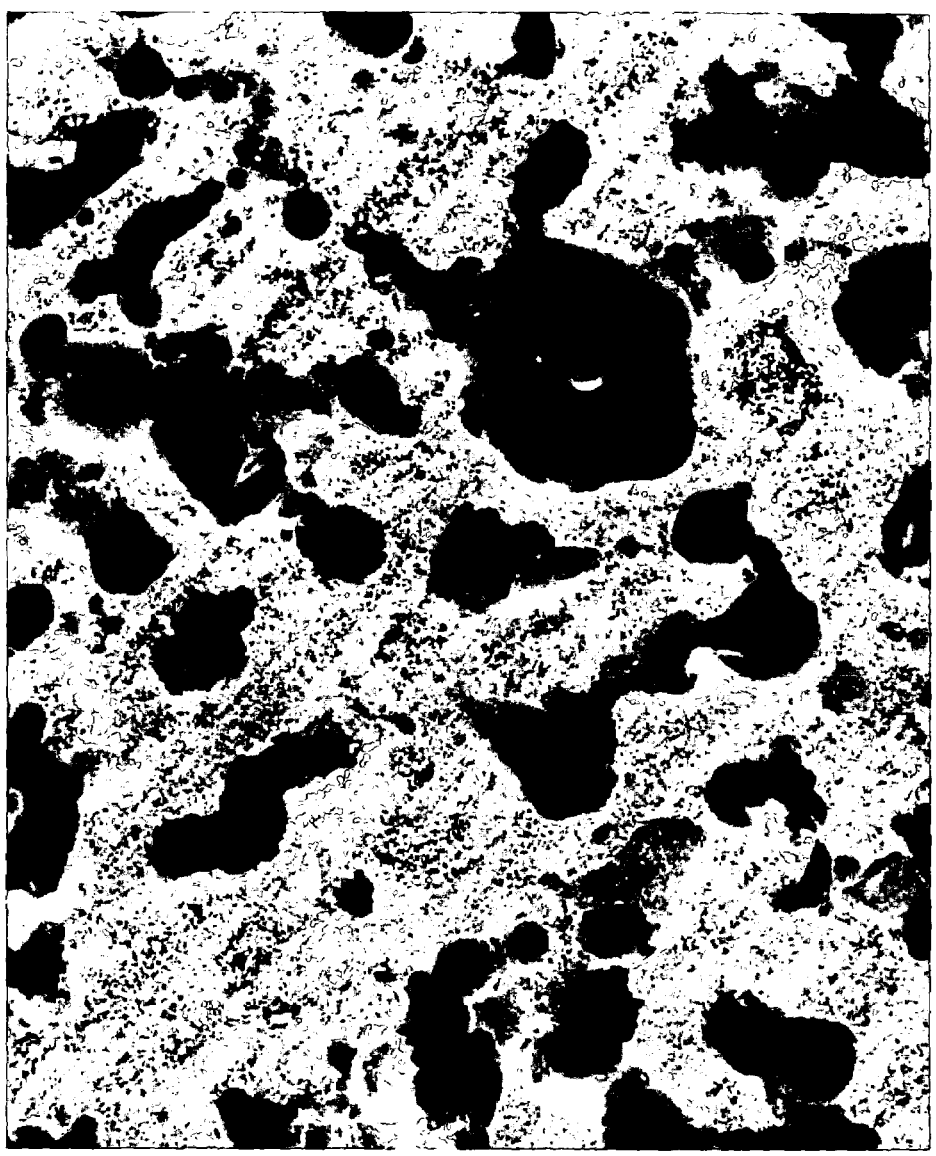
- FIG. 1 is a scanning electron microscopic (SEM) photograph illustrating the macropore of a β-TCP porous body obtained according to Example 1.

There will now be described various embodiments of the present invention will be explained.

The artificial bone according to one embodiment of the present invention contains a calcium phosphate-based ceramic porous body as a main component.

As already known, because of the fact that calcium phosphate compounds are provided with bone conduction property, calcium phosphate compounds have been conventionally employed as a component of artificial bone. Among the calcium phosphate compounds, apatite hydroxide (HAP) and β-tricalcium phosphate (β-TCP) are more excellent in bone conduction property and hence preferable for use as a component for the artificial bone.

Among them, β-TCP is not only excellent in especially bone conduction property but also provided with characteristics which enable the β-TCP to be absorbed into bone tissue. Namely, due to the characteristics of β-TCP, when the β-TCP is used to make up for a bone tissue, osteoblast takes advantage of the β-TCP to generate new bone and at the same time, the β-TCP is enabled to be absorbed by osteoclast, thus enabling the prosthesis portion to be replaced with time by autogenetic bone. Therefore, the β-TCP is an optimum material for use as a component of the artificial bone according to the present invention.

The bone conduction and bioabsorbability of calcium phosphate compounds vary greatly depending on the manufacturing process thereof. Thus, the β-TCP should preferably be one that can be obtained using, as a raw material powder, β-tricalcium phosphate powder which is synthesized by means of mechanochemical method where the raw material powder is wet-pulverized.

The β-TCP powder thus obtained is mixed with water, a deflocculant and a surfactant to form a slurry which is subsequently dried and sintered to form a ceramic porous body.

Next, the characteristics of porosity of the aforementioned calcium phosphate-based ceramic porous body will be explained.

The calcium phosphate-based ceramic porous body to be used for constituting an artificial bone or a tissue engineering carrier according to one embodiment of the present invention is required to be formed of a structure where a plurality of spherical or amoeba-like pores having a diameter ranging from 0.01 μm to 2000 μm, more preferably from 0.1 μm to 1000 μm are three-dimensionally distributed and interconnected with each other throughout the entire region of the porous body. By the phrase "spherical pores", it means a group of pores where a large number of spherical pores are interconnected with each other, and by the phrase "amoeba-like pores", it means pores where each of pores is elongated just like amoeba.

In this porous body, the pores having a larger diameter and falling on the macropore side are useful for the intrusion of cells as well as for the neogenesis of blood vessels after the implantation of artificial bone, while the pores having a smaller diameter and falling on the micropore side are useful for enhancing the affinity of the porous body to cells as well as for giving chemical stimulation (micro-elution of ions, etc.) to the surroundings.

Incidentally, the ceramic porous body to be employed in one embodiment of the present invention contains a plurality of interconnected pores whose diameters are distributed from 0.01 μm to 2000 μm, whereas the ceramic porous body that has been conventionally employed as an artificial bone includes a plurality of interconnected pores whose diameters are generally larger than 150 μm. Therefore, the ceramic porous body to be employed in one embodiment of the present invention can be fundamentally distinguished from the conventional ceramic porous body by the fact that the interconnected pores thereof are distributed also to far smaller side in pore size.

Further, in order to effectively achieve the formation of bone and the absorption of bone material in the employment of the ceramic porous body as an artificial bone and also in order to effectively achieve the formation of a composite with cultivated cells in the employment of the ceramic porous body as a tissue engineering carrier, the ceramic porous body is required to have a structure where a sufficient quantity of open pores which are interconnected with each other through interconnecting portions having a sufficiently large diameter are required to be distributed throughout the entire region of the ceramic porous body, i.e. from the outer surface to the core portion of the ceramic porous body.

Namely, it is important in this ceramic porous body to provide it with pores which are interconnected with each other through an interconnecting portion having a diameter of 100 μm or more and are distributed throughout the entire region of the porous body, i.e. from the core portion to outer surface portion of the porous body. By the phrase "interconnecting portion(s), it means a junction or junction portions formed between neighboring pores and having a smaller diameter than the diameter of the neighboring pores. Therefore, in order to allow living cells to invade into the interconnecting portions, it is important to make sure that the interconnecting portions have a sufficiently large diameter.

Therefore, the ceramic porous body to be employed in one embodiment of the present invention should preferably be constructed such that a total volume "A" of pores which are interconnected with each other through an interconnecting portion having a diameter of 100 μm or more throughout the entire region of the porous body is accounted for 5% or more, preferably 10% or more based on the entire volume of the porous body, and that the total volume "A" is accounted for 25% or more, preferably 30% or more based on a total volume of the pores having a pore diameter of 10 μm or more in the porous body. If the total volume "A" is less than 5% of the entire volume of the porous body, the quantity of pores which make it possible to allow cells to invade therein would become too small, so that it may become difficult to sufficiently generate the formation of bone, resulting in undesirable consequences.

Further, if the total volume "A" is less 25% based on a total volume of the pores having a pore diameter of 10 μm or more in the porous body, the quantity of pores which make it possible to allow cells to invade therein would become too small, so that it may become difficult to sufficiently generate the formation of bone, resulting in undesirable consequences.

Alternatively, the ceramic porous body to be employed in one embodiment of the present invention should preferably be constructed such that as a total volume of the pores which are interconnected with each other through an interconnecting portion having a diameter of "B" μm or more throughout the entire region of the porous body among the pores which are inter-connected with each other through an interconnecting portion having a diameter of 5 μm or more is defined as "C", a maximum value of the differential dC/dB is derived under a condition of: B>100 μm.

This differential dC/dB indicates the changes of the total volume of the interconnected pores relative to the changes of diameter of the interconnecting portions and means that the curve thereof has a peak in the region where the value of "B" exceeds over 100 μm.

In the case of the porous structure where a maximum value of the differential dC/dB can be derived under a condition where B is not more than 100 μm, the quantity of pores having a diameter of 100 μm or more in the diametral distribution of interconnecting portions would become insufficient and hence undesirable.

It is possible, through the employment of the aforementioned calcium phosphate-based ceramic porous body, to obtain an artificial bone which is capable of enabling living cells to smoothly invade into the porous body, of optimizing the affinity of the porous body to living cells, and of quickly achieving the formation of bone up to the core portion of the porous body.

For the purpose of promoting the quick formation of bone, a growth factor for promoting the formation of bone, a cell growth factor, hormone, etc may be incorporated in the aforementioned calcium phosphate-based ceramic porous body. Although there is not any particular limitation as long as the incorporating substance functions as a factor which is capable of promoting the formation of bone, BMP, FGF, TGF-β, PDGF, VEGF, IGF, HGF, PTH and estrogen may be incorporated in the aforementioned calcium phosphate-based ceramic porous body.

Further, when the aforementioned calcium phosphate-based ceramic porous body is employed as a tissue engineering carrier, the porous body is advantageous in the respect that cultivated cells can be quickly invaded into the porous body. In particular, when living cells which are capable of contributing the formation of bone, the remodeling of bone, and the metabolism of bone is incorporated in the aforementioned calcium phosphate-based ceramic porous body, it is possible to obtain an excellent artificial bone. As for the incorporating cells, there is not any particular limitation as long as they are capable of contributing the formation of bone, the remodeling of bone, and the metabolism of bone. For example, it is possible to employ, as incorporating cells, stem cell, marrow anaplostic cell, osteoblast, precursor cell of osteoblast, osteoclast and precursor cell of osteoclast. The stem cell to be incorporated may be those originating from bone marrow or various kinds thereof.

Next, the various examples of the present invention will be set forth, specifically explaining the effects of the present invention.

EXAMPLE 1

This example illustrates one manufacturing example of a porous body to be obtained through the employment of β-TCP as calcium phosphate-based ceramic.

The synthesis of the β-TCP was performed by means of mechanochemical method as follows. Namely, calcium carbonate powder and calcium hydrogen phosphate dihydrate powder were weighed at a molar ratio of 1:2 and placed, together with pure water, in a ball mill pot. Then, the resultant mixture was pulverized in a ball mill for about all day long to obtain a slurry. The resultant slurry was dried at a temperature of about 80° C. and then sintered at a temperature of about 750° C., thus obtaining powder which was found as being a high-purity β-TCP which was excellent in sintering property.

Then, water, an ammonium acrylate-based deflocculating agent and a polyoxyethylene alkylphenylether-based surfactant were added to this β-TCP powder and stirred to prepare a foamed slurry. The resultant foamed slurry was then allowed to dry and subsequently sintered at a temperature of 1050° C. to obtain a β-TCP porous body.

Figure 2:
FIG. 2 is a scanning electron microscopic (SEM) photograph illustrating the micropore of a β-TCP porous body obtained according to Example 1.

Photographs of this β-TCP porous body, which were obtained by means of scanning electron microscope (SEM) are shown in FIGS. 1 and 2. FIG. 1 shows the macropores and the interconnecting portions which were depicted by a magnification of 40 times and FIG. 2 shows the micropores which were depicted by a magnification of 10,000 times.

The characteristics of the pores of this porous body were evaluated. First of all, the weight and volume of the porous body were measured. Then, the porosity of the porous body was calculated by making use of these values thus measured, finding that the porosity thereof was found 75%. Further, as shown in FIG. 1, it was confirmed, through the observation using SEM, the existence of a large number of pores as macropores each having a diameter ranging from 100 to 400 μm.

The interconnecting property of pores as measured from outer environments was measured by making use of a mercury injecting method. Due to the measurement accuracy of the mercury injecting method, 100 μm is the upper limit in the evaluation of the diameter of the interconnecting portions. Therefore, it is possible, within this evaluation range, to measure the relationship between the diameter of the inter-connecting portions and the volume of entire pores which are communicated, through interconnecting portions having a larger diameter than the aforementioned value, with the outermost pores. The volume of entire pores which are interconnected through interconnecting portions having a diameter larger than 100 μm can be determined by a difference between the porosity and the quantity of mercury injected.

The measurement of the interconnecting property of pores of porous body by means of the mercury injecting method was performed in such a manner that a sample was dried in vacuum for 5 hours at a temperature of 110° C. as a pretreatment and the dried sample was taken out of the drying oven and allowed to cool spontaneously for about 30 minutes. The measurement was performed using Autopore IIIS 420 (trade name: Micromerities Co., Ltd.). As a result, the relationship between the diameter of the interconnecting portions and the volume of pores per unit volume (1 mL) of the porous body was found as shown in the following Table 1.

TABLE 1

| Diameter of communication portions (μm) | Volume of pores (mL) |
|---|---|
| >100 | 0.24 |
| 100–50 | 0.21 |
| 50–25 | 0.04 |
| 25–10 | 0.02 |
| 10–5 | 0 |
| 5> | 0.24 |

It will be seen from the results shown in above Table 1 that a total volume "A" of pores which were interconnected with each other through an inter-connecting portion having a diameter of 100 μm or more throughout the entire region of the porous body was 0.24 mL per unit volume of the porous body, which was equivalent to 24% per unit volume (1 mL) of the porous body. Further, it will be clearly admitted that the ratio of the total volume "A" to a total volume of the pores having a pore diameter of 10 μm or more in the porous body was 30% or more.

Moreover, it is clear that when a total volume of the pores which are interconnected with each other through an interconnecting portion having a diameter of "B" μm or more throughout the entire region of the porous body among the pores which are interconnected with each other through an interconnecting portion having a diameter of 5 μm or more throughout the entire region of the porous body is defined as "C", a maximum value of the differential dC/dB could be derived under a condition of: B>100 μm.

EXAMPLE 2

The β-TCP porous body (herein referred to as a sample "a") which was manufactured in Example 1 was implanted to make up for the thighbone of a rabbit to thereby evaluate the β-TCP porous body. As a control, the β-TCP powder prepared in the same manner as in Example 1 by means of mechanochemical method was mixed with a glycerin-based surfactant to obtain a mixture. By making use of this mixture, a porous body (herein referred to as a sample "b") was manufactured by means of the same wet foaming method as employed in the preparation of the sample "a" and was similarly implanted to make up for the thighbone of a rabbit to thereby evaluate the porous body.

Incidentally, this sample "b" was found to have a porosity of 75% which was the same as that of the sample "a" and a pore size ranging from 100 to 300 μm as observed by means of SEM. However, when the interconnecting property of the pores was evaluated by making use of the mercury injecting method, the value "A" illustrated in Example 1 was found very small (less than 10% of the volume of pores) and the maximum value of dC/dB was derived when B was 5 μm, thus indicating poor interconnecting property of the pores.

Further, a defective portion having a diameter of 5 mm and a length of 8 mm was formed at the condylus of the thighbone of a female rabbit weighing 3 kg and then, a sample of artificial bone having the same size as described above was implanted to make up for this defective portion. As a control, a defective portion of the same size as described above was formed in the thighbone of the rabbit and left unfilled with any artificial bone. Two weeks, four weeks and six weeks later, the prosthesis portion in each sample was taken out and a nondeashing sample was prepared and evaluated. Further, the area ratio of neogenetic bone (new bone) and the area ratio of the artificial bone in each of the samples were measured.

As a result, in the sample "a", the formation of bone extending from the peripheral portion toward the core portion of the artificial bone was found proceeded in an early stage of two-week period and the formation of bone was extended up to the core portion of the artificial bone in four-week period. Whereas, in the case of the sample "b", the formation of bone was recognized only at the peripheral portion of the artificial bone up to four-week period.

The area ratio of neogenetic bone (new bone) and the area ratio of the artificial bone in these samples are shown in the following Table 2.

TABLE 2

| Duration | Areal ratio of neogenetic bone (%) | | | Areal ratio of materials employe (%) | |
| --- | --- | --- | --- | --- | --- |
| (weeks) | Sample a | Sample b | Control | Sample a | Sample b |
| 2 W | 12 | 1.5 | 0 | 45 | 48 |
| 4 W | 23 | 6.7 | 0 | 18 | 33 |
| 6 W | 30 | 20 | 6.3 | 15 | 17 |

It was possible, through the results shown in Table 2, to confirm quick formation of new bone and the progress of absorption of the artificial bone. The reasons for these phenomena may be assumably attributed to the fact that the sample "a" was excellent in interconnecting property of pores.

EXAMPLE 3

A cell growth factor was incorporated in the β-TCP porous body (sample "a") which was manufactured in Example 1. As for the cell growth factor, rh BMP-2 was employed and dissolved in a buffering solution. The resultant solution was allowed to penetrate into the porous body so as to fill the porous body with the solution at a ratio of 10 to 1000 μg per 1 $cm^3$ of the porous body. The resultant porous body was dried in vacuum or lyophilized, thus obtaining an artificial bone.

This artificial bone was found excellent in affinity with living cells and capable of permitting living cells to smoothly enter into the inner portion of the artificial bone. At the same time, this artificial bone was found excellent in promoting the propagation of living cells.

EXAMPLE 4

Cultivated cells were incorporated in the β-TCP porous body (sample "a") which was manufactured in Example 1, and the resultant body was subsequently evaluated. As a control, cultivated cells were incorporated in the sample "b" shown in Example 2 in the same manner as the sample "a", and the resultant body was subsequently evaluated.

First of all, bone marrow cells were collected from the thighbone of Fisher's rat and then, subjected to initial cultivation for 8 days by making use of MEM culture medium containing 15% of FBS. Thereafter, the cells were peeled off by treating them with trypsin and formed into a cell-floating solution containing the cells at a concentration of $10^6$/mL. This cell-floating solution was then allowed to penetrate into the β-TCP porous bodies of samples "a" and "b", respectively. Thereafter, 10 mM of dexamethasone, 10 mM of β-glycerophosphate and 50 μg/mL of ascorbic acid were additionally added to these β-TCP porous bodies to cultivate the cells for two weeks. Then, the resultant β-TCP porous bodies were respectively subcutaneously implanted in the back of the Fisher's rat to evaluate the porous bodies.

When these samples were observed by means of SEM before the subcutaneous implantation thereof, the cultivated cells were found penetrated in the core portion of the porous body in the case of the sample "a". Whereas, in the case of the sample "b", the penetration of the cultivated cells could not be observed. Further, at the moment four weeks after the subcutaneous implantation of the cultivated cells, ectopic bone formation was recognized in the core portion of the porous body in the case of the sample "a", but such a formation of the bone was not recognized in the case of the sample "b".

It was possible, from the aforementioned results, to confirm that the sample "a" was excellent in interconnecting property of pores and capable of enabling living cells to smoothly penetrate therein even in vitro.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An artificial bone comprising a calcium phosphate-based ceramic porous body having a plurality of spherical or amoeba-like pores which are three-dimensionally distributed throughout an entire region of the porous body, are interconnected with each other, and each has a diameter ranging from 0.01 μm to 2000 μm, the porous body having a porous structure in which a total volume "A" of pores which are interconnected with each other through an interconnecting portion having a diameter of 100 μm or more from a core portion to outer surface portion of the porous body is accounted for 5% or more based on an entire volume of the porous body and the total volume "A" is accounted for 25% or more based on a total volume of the pores having a pore diameter of 10 μm or more in the porous body, or a porous structure in which a total volume of the pores interconnected with each other through an interconnecting portion having a diameter of "B" μm or more from a core portion to outer surface portion of the porous body among the pores interconnected with each other through an interconnecting portion having a diameter of 5 μm or more is defined as "C", and a maximum value of differential dC/dB is derived under a condition of: B>100 μm.

2. The artificial bone according to claim 1, wherein the calcium phosphate-based ceramic is selected from the group consisting of β-tricalcium phosphate, apatite hydroxide, ceramics comprising β-tricalcium phosphate and apatite hydroxide, and crystallized glass.

3. The artificial bone according to claim 2, wherein the calcium phosphate-based ceramic is obtained using β-tricalcium phosphate powder which is synthesized by means of mechanochemical method.

4. The artificial bone according to claim 2, wherein the calcium phosphate-based ceramic is obtained using β-tricalcium phosphate powder which is synthesized by means of mechanochemical method, wherein the β-tricalcium phosphate powder is mixed with water, a deflocculant and a surfactant to form a slurry which is subsequently dried and sintered to form the calcium phosphate-based ceramic.

5. The artificial bone according to claim 1, wherein at least one substance selected from the group consisting of BMP, FGF, TGF-β, PDGF, VEGF, IGF, HGF, PTH and estrogen is incorporated in the calcium phosphate-based ceramic porous body.

6. A tissue engineering carrier which is capable of tissue engineeringly incorporating living cells, and comprises a calcium phosphate-based ceramic porous body having a plurality of spherical or amoeba-like pores which are three-dimensionally distributed throughout an entire region of the porous body, are interconnected with each other, and each has a diameter ranging from 0.01 μm to 2000 μm, the porous body having a porous structure in which a total volume "A" of pores which are interconnected with each other through an interconnecting portion having a diameter of 100 μm or more from a core portion to outer surface portion of the porous body is accounted for 5% or more based on an entire volume of the porous body and the total volume "A" is accounted for 25% or more based on a total volume of the pores having a pore diameter of 10 μm or more in the porous body, or a porous structure in which a total volume of the pores interconnected with each other through an interconnecting portion having a diameter of "B" μnm or more from a core portion to outer surface portion of the porous body among the pores interconnected with each other through an interconnecting portion having a diameter of 5 μm or more is defined as "C", and a maximum value of differential dC/dB is derived under a condition of: B>100 μm.

7. The tissue engineering carrier according to claim 6, wherein the calcium phosphate-based ceramic is selected from the group consisting of β-tricalcium phosphate, apatite hydroxide, ceramics comprising β-tricalcium phosphate and apatite hydroxide, and crystallized glass.

8. The tissue engineering carrier according to claim 7, wherein the calcium phosphate-based ceramic is obtained using β-tricalcium phosphate powder which is synthesized by means of mechanochemical method.

9. The tissue engineering carrier according to claim 7, wherein the calcium phosphate-based ceramic is obtained using β-tricalcium phosphate powder which is synthesized by means of mechanochemical method, wherein the β-tricalcium phosphate powder is mixed with water, a deflocculant and a surfactant to form a slurry which is subsequently dried and sintered to form the calcium phosphate-based ceramic.

10. An artificial bone wherein at least one kind of cell selected from the group consisting of stem cell, marrow anaplostic cell, osteoblast, precursor cell of osteoblast, osteoclast and precursor cell of osteoclast is incorporated in the tissue engineering carrier claimed in claim 6.

* * * * *